United States Patent
Koh

(10) Patent No.: US 8,249,706 B2
(45) Date of Patent: *Aug. 21, 2012

(54) ADAPTIVE RATE PROGRAMMING CONTROL IN IMPLANTABLE MEDICAL DEVICES USING VENTRICULAR-ARTERIAL COUPLING SURROGATES

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 324 days.

This patent is subject to a terminal disclaimer.

(21) Appl. No.: 12/694,098

(22) Filed: Jan. 26, 2010

(65) Prior Publication Data

US 2011/0184485 A1    Jul. 28, 2011

(51) Int. Cl.
*A61N 1/365*    (2006.01)
(52) U.S. Cl. .......................................... 607/18
(58) Field of Classification Search ............... 607/16–18
See application file for complete search history.

(56) References Cited

U.S. PATENT DOCUMENTS
2011/0028801 A1 * 2/2011 Koh .............................. 600/301

FOREIGN PATENT DOCUMENTS
WO    2008103078 A1    8/2008
* cited by examiner

*Primary Examiner* — Carl H Layno
*Assistant Examiner* — Paula J Stice

(57) ABSTRACT

Selection of an appropriate rate programming control (RPC) setting in an implantable medical device (IMD), uses analysis of VA coupling surrogate conditions. The VA coupling surrogate conditions are derived from signals such as cardiogenic impedance, blood pressure, and the pulsatile components of PPG. By analyzing a waveform of the measured surrogate condition, the IMD estimates wall stiffness, through the slope of the waveform, and peripheral arterial pressure, through the reflection time between the main wave and reflection wave of the waveform. These values are plotted against each other on a VA coupling coordinate plane. Based on the location and orientation of the resulting VA coupling plot, the IMD selects an appropriate RPC setting.

20 Claims, 10 Drawing Sheets

ADAPTIVE RATE PROGRAMMING CONTROL IN IMPLANTABLE MEDICAL DEVICES USING VENTRICULAR-ARTERIAL COUPLING SURROGATES

FIELD OF THE DISCLOSURE

The present disclosure relates, in general, to implantable cardiac devices and, more particularly, to adaptive rate programming control (RPC) in implantable medical devices (IMD) using ventricular-arterial (VA) coupling surrogates.

BACKGROUND

An implantable medical device (IMD), such as a pacemaker and/or implantable cardioverter-defibrillator (ICD), regulates or synchronizes the beating of the heart with electrical impulses, delivered by electrodes contacting the heart muscles. Some IMDs include a number of different sensors and logic allowing them to monitor the rate and rhythm of the heart as well as to measure various cardiac surrogates that provide information on the operation of the heart.

One of the primary purposes of such IMDs is to maintain an adequate heart rate in chronotropic incompetent patients. Chronotropic incompetence is generally considered the inability of a patient to achieve an adequate heart rate in response to physiological need, such as during exercise. Such chronotropic incompetence may be due to the heart's natural pacemaker being inadequate, problems with the heart's electrical conduction system, age, medication, and the like. However, treatment of chronotropic deficiencies using an IMD is not always a simple matter of firing off the heart to beat at a certain time. It often includes the complex synchronization of the individual movements and processes that make up each stage of a typical heart beat. As measurements are made and analyzed by the IMD, electrical therapies may be delivered when the performance or synchronization of the heart varies from some pre-defined measurement of normal operation.

Because each patient's heart and circulatory system is different and may have different physiological responses over time even within its own operation, programmable fixed-rate systems generally do not provide optimal or sometimes even adequate treatment to patients. In response, rate responsive pacemaker systems have been developed which typically include some means or methods for monitoring at least one patient-specific variable. Based on this patient-specific variable, the IMD can determine an indicated pacing rate as a function of the sensed pacing variable. This rate responsive system, referred to herein as rate programming control (RPC), allows the IMD to optimally control pacing rate in terms of the patient's condition. Thus, such RPC functionality generally provides an improved response to the patient's physiological needs, as compared to programmable fixed rate pacemakers.

One of the ultimate goals of such IMDs is to increase a patient's cardiac output in order to meet the patient's physiological needs. The presumption for such treatment is that increasing the heart rate will boost the cardiac output by increasing the stroke volume. Stroke volume is the amount of blood pumped by the ventricle during each beat cycle. It is equal to the difference between the end diastolic volume (EDV) (the volume of blood in the ventricle at its most full) and the end systolic volume (ESV) (the volume of blood remaining in the ventricle after it completes contraction). Under normal physiological conditions, increasing heart rate will naturally increase the level of ventricular contractile force (i.e., contractility). This force-frequency relationship is known as the Treppe effect. However, increasing the heart rate without considering peripheral resistance may cause ischemia/infarction or atrial fibrillation.

SUMMARY

The present disclosure is directed to selecting appropriate RPC settings in an IMD using analysis of VA coupling surrogate conditions, such as cardiogenic impedance, blood pressure, and the pulsatile components of PPG. By analyzing the waveform of the measured surrogate condition, the IMD estimates wall stiffness, through the slope of the waveform, and peripheral arterial pressure, through the reflection time between the main wave and reflection wave of the waveform. These values are plotted against each other on a VA coupling coordinate plane. Based on the location and orientation of the resulting plot, the IMD selects an appropriate RPC setting.

Representative embodiments of the present teachings are directed to methods for selecting an RPC setting in an IMD. The methods include detecting an increase in activity for the IMD patient, estimating a cardiac wall stiffness over a predetermined period, and estimating an peripheral arterial pressure over the same predetermined period. Responsive to the estimated cardiac wall stiffness and estimated peripheral arterial pressure, the IMD selects the RPC setting.

Additional representative embodiments of the present teachings are directed to IMDs that include an activity sensor, at least one cardiac pacing lead, at least one VA coupling surrogate condition sensor, and a programmable microcontroller coupled to the activity sensor, to the cardiac pacing lead, and to the VA coupling surrogate condition sensor. The programmable microcontroller controls operation of the IMD. The IMD also includes a memory coupled to the programmable microcontroller and a VA coupling surrogate analysis module stored on the memory. When executed by the programmable microcontroller, the surrogate analysis module configures the IMD to activate the activity sensor to detect an increase in activity of a patient, and to activate the surrogate condition sensor. The activated surrogate condition sensor is controlled to estimate a cardiac wall stiffness over a predetermined period and estimate an peripheral arterial pressure over the same predetermined period. The IMD is further configured by the executing VA coupling surrogate analysis module to generate a VA coupling plot of the estimated cardiac wall stiffness values against the estimated peripheral arterial pressure values and to select an RPC setting based on a location and an orientation of the VA coupling plot.

Further representative embodiments of the present teachings are directed to systems for selecting an RPC setting in an IMD. These systems include means for detecting an increase in activity for a patient having the IMD, means for estimating a cardiac wall stiffness over a predetermined period, means for estimating an peripheral arterial pressure over the predetermined period, and means for generating a VA coupling plot of the estimated cardiac wall stiffness values against the estimated peripheral arterial pressure values. The systems also include means, executable responsive to a location and an orientation of the VA coupling plot, for selecting the RPC setting.

The foregoing has outlined rather broadly the features and technical advantages of the present teachings in order that the detailed description of the teachings that follows may be better understood. Additional features and advantages of the teachings will be described hereinafter which form the subject of the claims of the teachings. It should be appreciated by those skilled in the art that the conception and specific embodiment disclosed may be readily utilized as a basis for modifying or designing other structures for carrying out the same purposes of the present teachings. It should also be realized by those skilled in the art that such equivalent constructions do not depart from the spirit and scope of the teachings as set forth in the appended claims. The novel features which are believed to be characteristic of the teachings, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present teachings.

BRIEF DESCRIPTION OF THE DRAWINGS

For a more complete understanding of the present teachings, reference is now made to the following descriptions taken in conjunction with the accompanying drawing.

DETAILED DESCRIPTION

The following description includes the best mode presently contemplated for practicing the present teachings. The description is not to be taken in a limiting sense but is merely for the purpose of describing the general principles of the illustrative embodiments. The scope of the present teachings should be ascertained with reference to the claims. In the description that follows, like numerals or reference designators will refer to like parts or elements throughout.

Overview of Implantable Devices

Figure 1:
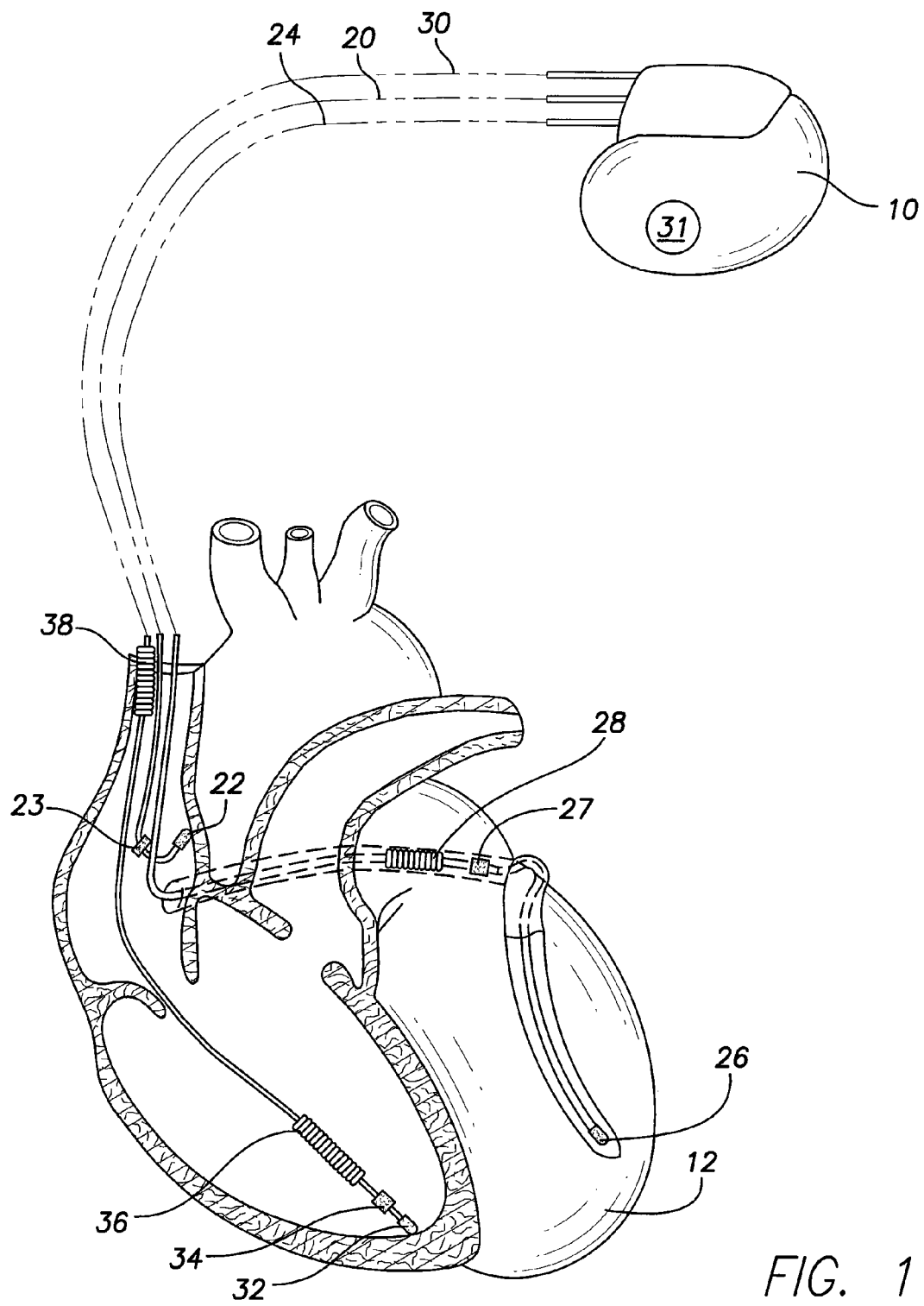
FIG. 1 is a diagram illustrating a stimulation device in electrical communication with the heart of a patient by way of three leads suitable for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode 31 can be provided in proximity to the device can.

Figure 2A:
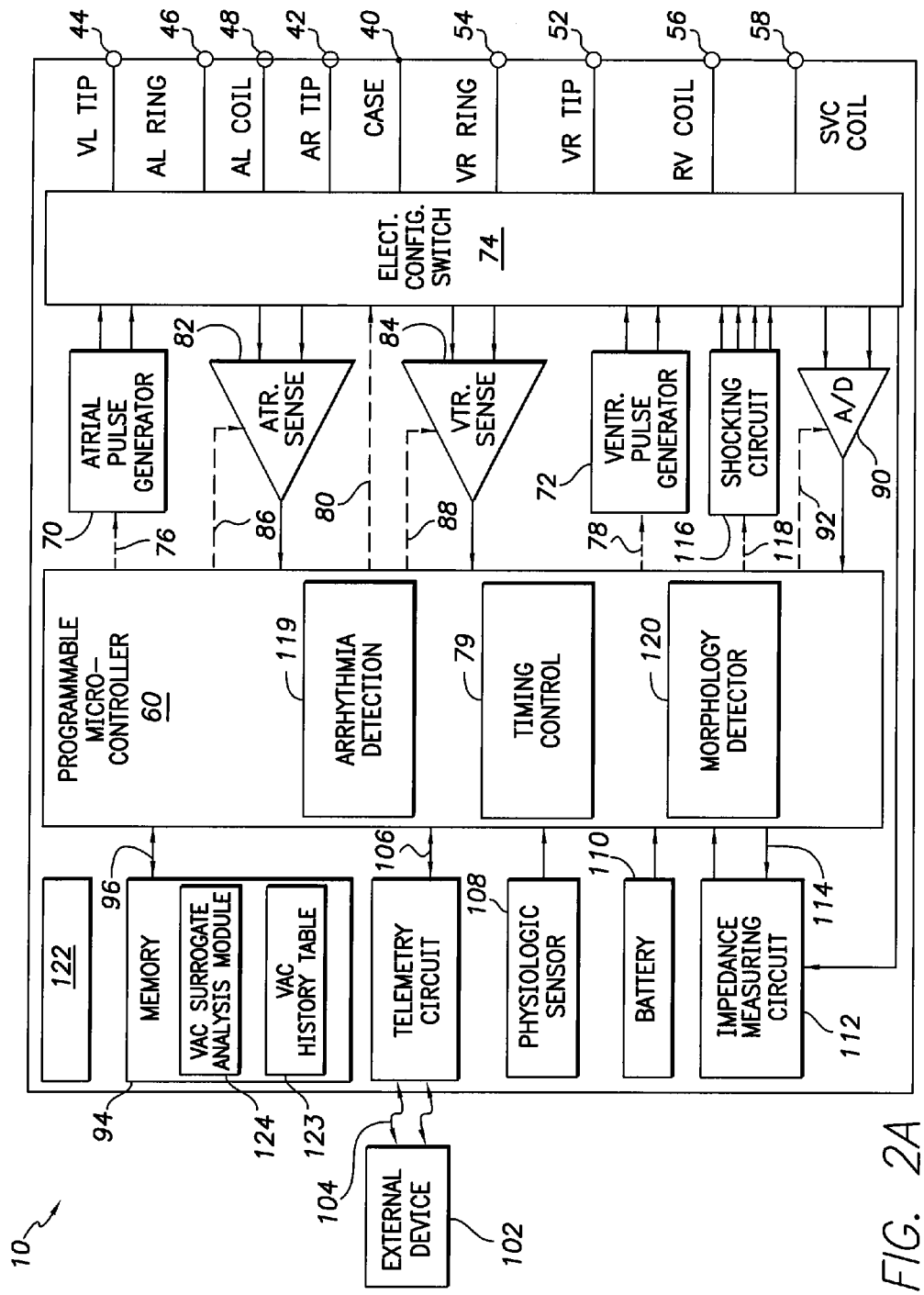
FIG. 2A is a simplified block diagram illustrating an implantable stimulation device configured as a system in which the various embodiments of the present teachings may operate.

As illustrated in FIG. 2A, a simplified block diagram is shown of the multi-chamber implantable stimulation device 10, which is capable of treating both fast and slow arrhythmias with stimulation therapy, including cardioversion, defibrillation, and pacing stimulation. The stimulation device 10 is configured as a system in which the various embodiments of the present teachings may operate. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2A, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, (FIG. 1) for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals).

As such, to achieve right atrial sensing and pacing, the connector includes at least a right atrial tip terminal (AR TIP) 42 adapted for connection to the atrial tip electrode 22 (FIG. 1) and a right atrial ring (AR RING) electrode (not shown) adapted for connection to the right atrial ring electrode 23 (FIG. 1). To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26 (FIG. 1), the left atrial tip electrode 27 (FIG. 1), and the left atrial coil electrode 28 (FIG. 1), respectively. To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit 122 generates a signal for an additional terminal (not shown) for connection to the vibratory alert electrode 31 (FIG. 1). In one embodiment, the vibratory alert will alert the patient, and then a home monitor can be used to transfer the information associated with the alert from the device 10 to an attending medical professional, who can take the appropriate clinical action.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of the memory. The details of the design and operation of the microcontroller 60 are not critical to the present teachings. Rather, any suitable microcontroller 60 may be used that carries out the functions described. The use of microprocessor-based control circuits for performing timing and data analysis functions are well known in the art.

As shown in FIG. 2A, an atrial pulse generator 70 and a ventricular pulse generator 72 generate pacing stimulation pulses for delivery by the right atrial lead 20 (FIG. 1), the right ventricular lead 30 (FIG. 1), and/or the coronary sinus lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., as is well known in the art. The switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the coronary sinus lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fibwaves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (A/D) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the coronary sinus lead 24 (FIG. 1), and the right ventricular lead 30 (FIG. 1) through the switch 74 to sample cardiac signals across any pair of desired electrodes. The controller 60 controls the data acquisition system via control signals 92.

The microcontroller 60 is further coupled to a memory 94 by a suitable data/address bus 96. The programmable operating parameters used by the microcontroller 60 are stored and modified, as required, in order to customize the operation of the stimulation device 10 to suit the needs of a particular patient. The memory 94 includes software modules, such as the ventricular-arterial (VA) coupling surrogate analysis module 124 and the VA coupling history table 123, which, when executed or used by the microcontroller 60, provide the operational functions of the implantable stimulation device 10. Additional operating parameters and code stored on the memory 94 define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In one embodiment, the stimulation device 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2A. For the stimulation device 10, which employs shocking therapy, the battery 110 is capable of operating at low current drains for long periods of time, and is capable of providing high-current pulses (for capacitor charging) when the patient requires a shock pulse. The battery 110 also has a predictable discharge characteristic so that elective replacement time can be detected. In one embodiment, the device 10 employs lithium/silver vanadium oxide batteries. As further shown in FIG. 2A, the device 10 has an impedance measuring circuit 112 enabled by the microcontroller 60 via a control signal 114.

In the case where the stimulation device 10 is intended to operate as an IMD, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28 (FIG. 1), the RV coil electrode 36 (FIG. 1), and/or the SVC coil electrode 38 (FIG. 1). As noted above, the housing 40 may function as an active electrode in combination with the RV coil electrode 36 (FIG. 1), or as part of a split electrical vector using the SVC coil electrode 38 (FIG. 1) or the left atrial coil electrode 28 (FIG. 1) (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an arrhythmia detection control 119 that analyzes the sensed electrical signals to determine whether or not arrhythmia is being experienced.

Figure 2B:
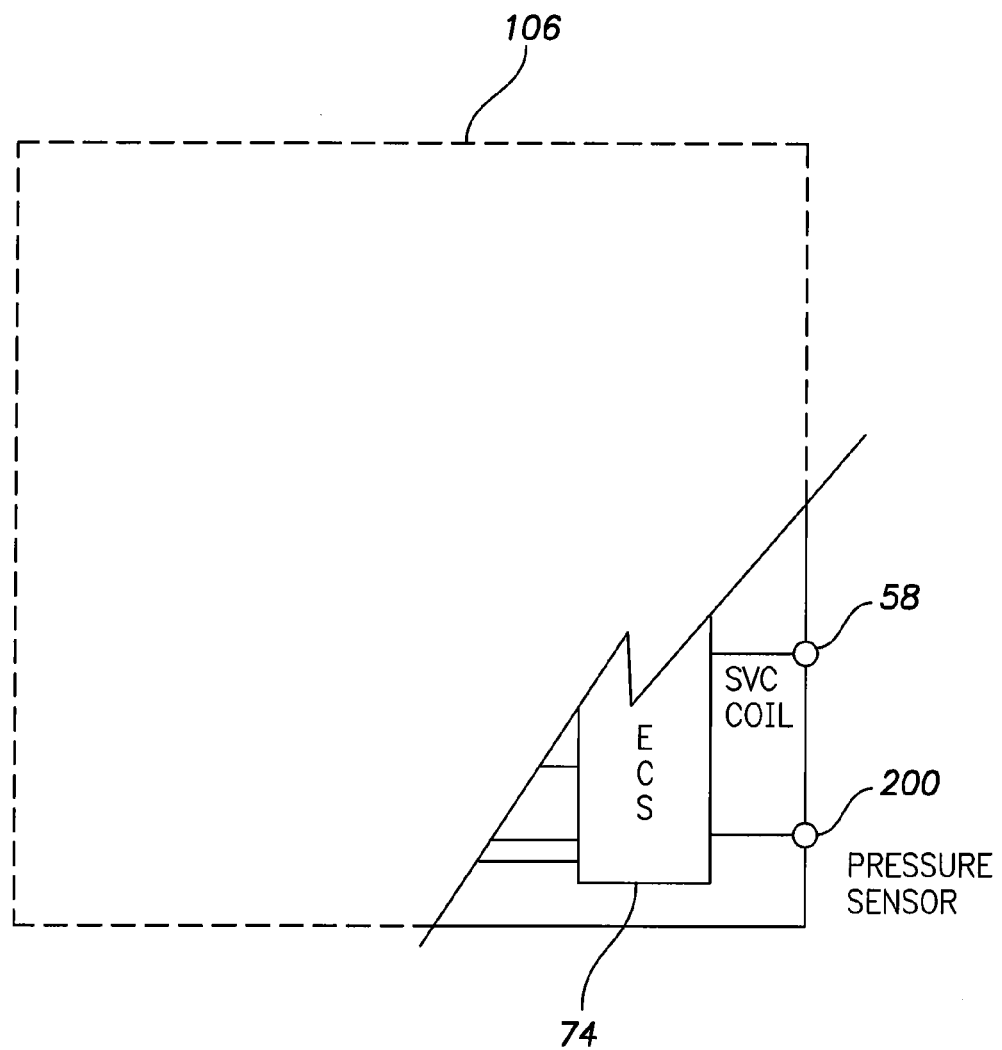
FIG. 2B is a block diagram illustrating partial detail of a stimulation device 10b configured as a system in which the various embodiments of the present teachings may operate.

FIG. 2B is a block diagram illustrating partial detail of a stimulation device 10b configured as a system in which the various embodiments of the present teachings may operate. The stimulation device 10c includes each of the features illustrated with regard to the stimulation device 10 (FIG. 2A), and, as such, the majority of detail is hidden in FIG. 2B for the sake of clarity. The illustrated portion of the stimulation device 10c provides the addition of a pressure sensor 200 connected to the electrical configuration switch 74, along with the remaining contacts, such as the SVC coil 58. The pressure sensor 200 allows the stimulation device 10b to conduct cardiac output measurements using atmospheric pressure readings in blood vessels and calculations based on principles of fluid dynamics. The operation of these devices will be described below with reference to the remaining figures.

The remaining figures, flow charts, graphs and other diagrams illustrate the operation and novel features of the stimulation device 10 as configured in accordance with exemplary embodiments of the present teachings. In the flow chart, the various process steps are summarized in individual "blocks." Such blocks describe specific actions or decisions made or carried out as the process proceeds. Where a microcontroller (or equivalent) is employed, the functional block diagrams provide the basis for a "VA coupling analysis process" that may be used by such a microcontroller (or equivalent) to adaptively select RPC settings in IMD patients. Those skilled in the art may readily write such a program based on the functional block diagrams and other descriptions presented herein.

Determining Adaptive Rate Programming Control (RPC) Using Surrogates of Ventricular-Arterial Coupling As previously noted, when physiological conditions are normal, the presumptions of a normal force-frequency relationship are valid. However, when physiological conditions are diminished or abnormal, such as with heart failure patients or patients having vessels stiffened by calcification or arteriosclerosis, the same presumptions are not reliable. For example, when the myocardium has deteriorated causing a stiffening of the ventricular walls, there is an "inverse" Treppe effect. That is, in heart failure cases having an increased stiffness in the cardiac walls, an increase in the frequency, i.e., heart rate, actually results in a decrease in contractility of the ventricle. Therefore, increasing the heart rate in such heart failure patients may generally decrease cardiac output and likely places the patient in danger of a catastrophic cardiac failure event. Similarly, heart failure patients that have thickening or narrowing of the arteries will also not generally have increased cardiac output with an increased heart rate. The thickening or narrowing of the arteries increases the peripheral pressure between the ventricle and the artery. The increased peripheral pressure makes it harder for the ventricle to pump the blood into the artery and increases the amount of blood that "backflows" or reflects off the stiffened or narrowed artery back into the ventricle because of the backward pressure exerted by the artery. This regurgitation raises the baseline end systolic volume (ESV), which can lead to pulmonary edema and respiratory failure if left untreated. In addition, even if the cardiac output (CO) increases, blood is not adequately delivered to the periphery where oxygen is needed.

Because of these exceptions to the general force-frequency relationship rules, the measurement of stroke volume, as an indicator of cardiac output or cardiac performance, is an inadequate variable for determining pacing or resynchronization rates in RPC-enabled IMDs. Instead, the ejection fraction provides a better measurement of the volume of blood the ventricle can actually pump based on the coupling relationship between the heart and the body's systemic vasculature. The ejection fraction is determined as a ratio of the stroke volume to the end diastolic volume (EDV) according to the following formula:

$$EF = \frac{SV}{EDV} = \frac{(EDV - ESV)}{EDV} \quad (1)$$

where EF is the ejection fraction and SV is the stroke volume. As formula (1) indicates, if the baseline ESV increases because the arterial wall-thickness or stiffness causes increased backflow or because the ventricular wall stiffness decreases the contractility or pumping force of the ventricle, then the ejection fraction (EF) will decrease. However, while EF provides a more accurate indicator of the overall operation of the heart by including the effects of ventricular and arterial physiology, the EF, by itself, cannot provide sufficient detail for purposes of selecting an adequate RPC setting.

The interaction between the heart and the systemic vasculature is known as ventricular-arterial (VA) coupling and is an important determinant of cardiovascular performance. The EF measurement takes into account the effects of VA coupling, but does not provide details of VA coupling. The capacity of the body to increase cardiac output, regulate systemic blood pressure, and respond appropriately to elevations in heart rate and preload depends on both the properties of the heart and the properties of the vasculature into which the heart ejects blood. Therefore, a measure or determination of VA coupling may be accomplished by an IMD monitoring the ventricular wall stiffness and arterial vascular impedance, i.e., arterial wall stiffness or peripheral pressure and adaptively selecting RPC settings accordingly.

Figure 3:
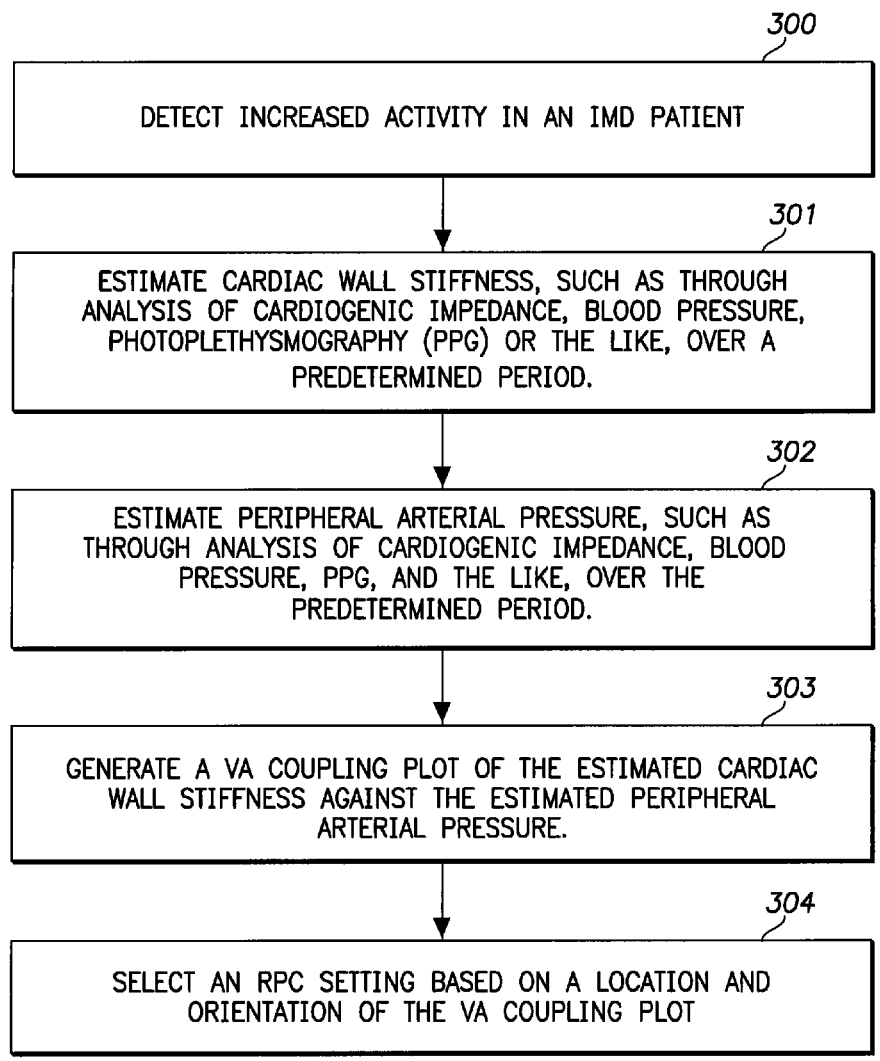
FIG. 3 is a functional block diagram illustrating functional blocks included in one embodiment of the present teachings.

FIG. 3 is a functional block diagram illustrating functional blocks included in one embodiment of the present teachings. In block 300, the IMD detects an increase in activity in the patient. The IMD estimates cardiac wall stiffness, in block 301, through analysis of surrogate variables, such as cardiogenic impedance, blood pressure, photoplethysmography (PPG), or the like, over a predetermined period. The IMD also estimates the peripheral arterial pressure, in block 302, over the same predetermined period using analysis of the same surrogates, i.e., cardiogenic impedance, blood pressure, PPG, or the like, over the same predetermined period. In block 303, the IMD generates a VA coupling plot relating the estimated cardiac wall stiffness values against the estimated peripheral arterial pressure values. The IMD may then select an appropriate RPC setting, in block 304, based on a location and orientation of the VA coupling plot.

The various embodiments of the present teachings benefit because the cardiac wall stiffness and peripheral arterial pressure may be determined by measuring and analyzing a single surrogate variable. For example, an IMD configured according to an embodiment of the present teachings may estimate the cardiogenic impedance of the heart cycles and, by analyzing different portions of the single cardiogenic impedance estimation, may determine values for both wall stiffness and peripheral pressure.

Figure 4A:
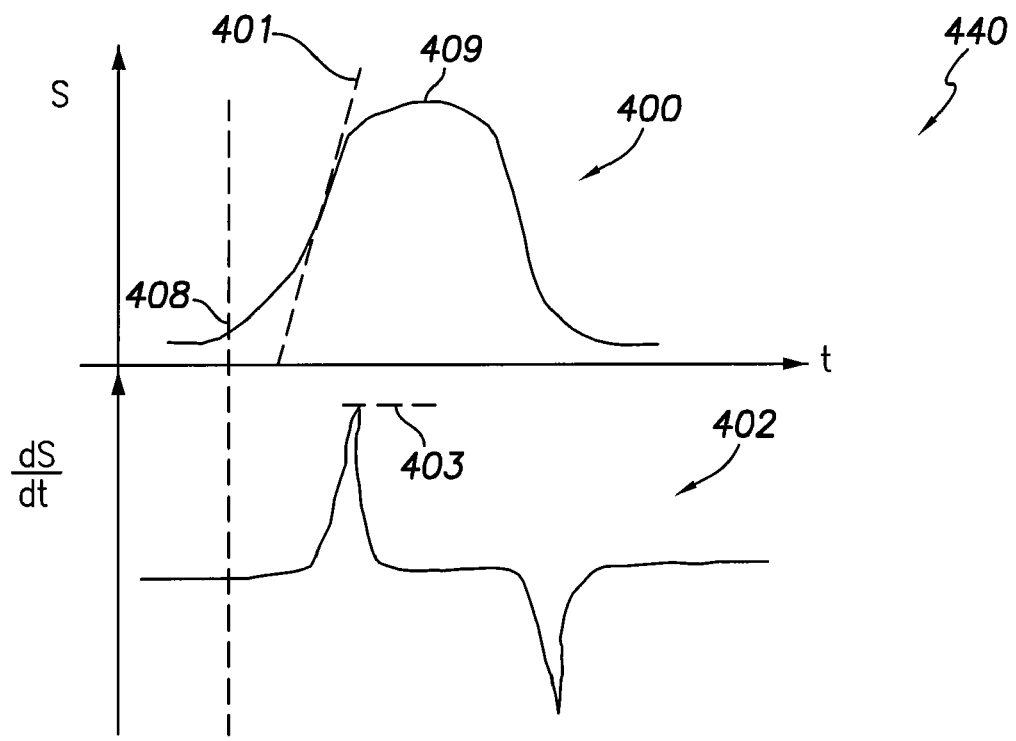
FIG. 4A is a surrogate condition graph generated by an IMD configured according to one embodiment of the present teachings.

FIG. 4A is a surrogate condition graph 440 generated by an IMD configured according to one embodiment of the present teachings. The surrogate condition graph 440 includes a measured S waveform 400 and a first derivative dS/dt graph 402. The measured surrogate variable, S, represents the surrogate condition used for determination of the cardiac wall stiffness and peripheral arterial pressure. While the generic surrogate variable S is used for clarity of explanation, it should be understood that, depending on the particular embodiment of the present teachings, S represents a surrogate condition, such as cardiogenic impedance, blood pressure, the pulsatile component of a PPG, or the like. Each of these specific surrogate conditions results in a waveform graph that is similar in appearance and in physiological response to the measured S waveform 400.

The measured S waveform 400 represents a typical measurement for the surrogate condition. At point 408, the ventricle has contracted and is in its "empty" state, i.e., has the least amount of blood present. As the ventricle relaxes and expands, blood is pumped and drawn into the ventricle from the atrium until point 409 is reached. Point 409 is the "full" state, i.e., has the most amount of blood present. The speed at which the ventricle can transition from point 408 to point 409 provides an indication of the contractility of the ventricular wall and, thus, the cardiac wall stiffness. A measurable value of this speed is the slope 401 of the measured S waveform 400. The slope 401, therefore, provides a measurement of contractility or cardiac wall stiffness. The first derivative of the measured S waveform 400 provides the means to calculate the slope. The IMD obtains the measured S waveform 400 and calculates the first derivative dS/dt graph 402 to obtain the derived slope 403. The derived slope 403 is then recorded as the cardiac wall stiffness value for this measurement point.

Figure 4B:
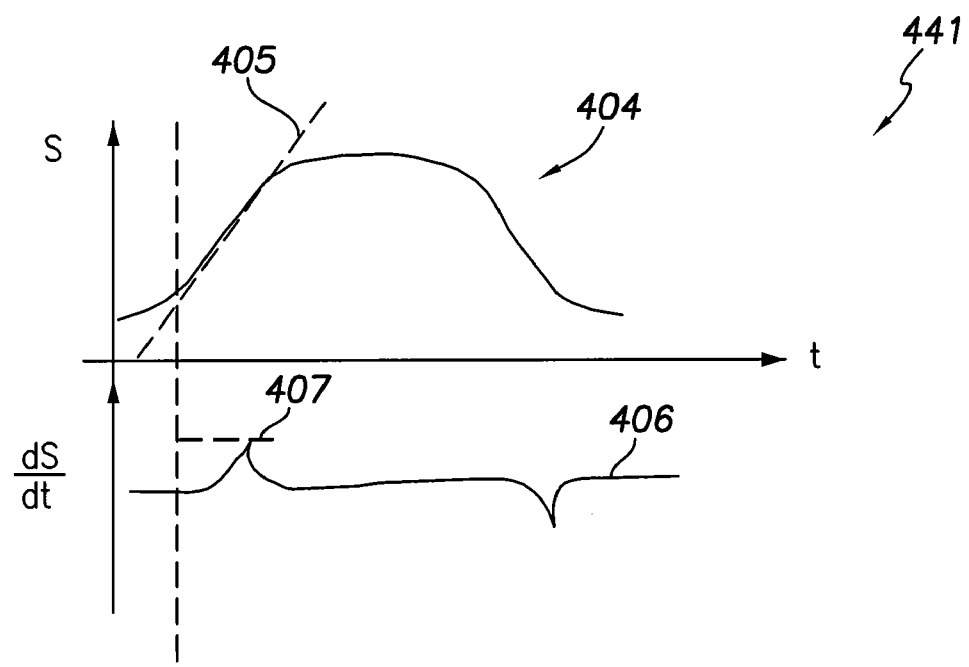
FIG. 4B is a surrogate condition graph generated by an IMD configured according to one embodiment of the present teachings.

FIG. 4B is a surrogate condition graph 441 generated by an IMD configured according to one embodiment of the present teachings. The surrogate condition graph 441 includes a measured S waveform 404 and a first derivative dS/dt graph 406. In viewing the measured S waveform 404, the slope 405 is much lower than the slope 401 (FIG. 4A). The lower value of the slope 405 would indicate that it takes longer for the ventricle to transition from its empty state to its full state. Calculation of the first derivative dS/dt graph 406 by the IMD confirms the lower derived slope 407. The lower value of the derived slope 407 provides an indication of the change in contractility of the ventricular wall. Depending on when that change occurs and how much the change is, it may represent a normal response or an abnormal response. The derived slope 407 is then recorded as the cardiac wall stiffness value for another measurement point.

Figure 5A:
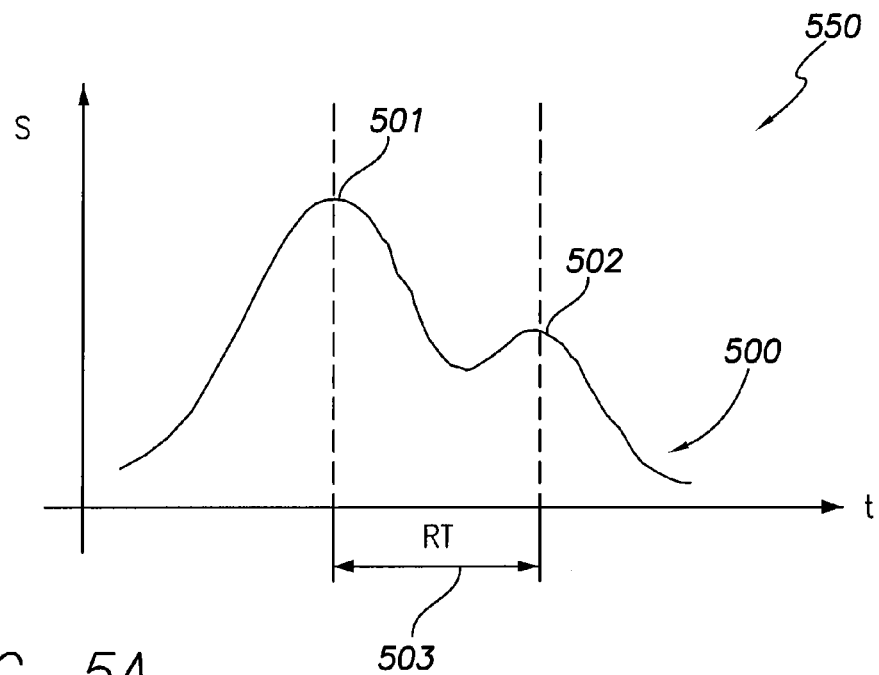
FIG. 5A is a surrogate condition graph measured by an IMD configured according to one embodiment of the present teachings.

At the same time that the IMD is measuring and analyzing the surrogate condition for an estimate of the cardiac wall stiffness or contractility, it also analyzes a surrogate condition for peripheral arterial pressure. FIG. 5A is a surrogate condition graph 550 measured by an IMD configured according to one embodiment of the present teachings. The graphical appearance of the surrogate condition graphs 440 and 441 illustrated in FIGS. 4A and 4B are idealized graphs intended to show the basic shape of the measured surrogate condition. However, the actual shape of the measured surrogate is more accurately reflected in the measured S waveform 500. As is apparent from the appearance of the measured S waveform 500, the surrogate waveform includes two predominant peaks, peaks 501 and 502. The peak 501 represents the main waveform resulting from the pumping action of the ventricle. However, the peak 502 represents a reflection wave caused by any impedance mismatch between the ventricle and the artery.

Reflection waves occur in various flow systems, whether physical flow systems or electrical flow, i.e., current, systems. When there is an impedance mismatch between one position in the flow system and another, there is an increase in pressure that occurs at the transition point. In consideration of the cardiac system, an impedance mismatch may occur between the ventricle and the artery into which the ventricle pumps blood. The ventricle pumps a certain volume of blood into the artery when the artery provides a certain peripheral pressure. If that peripheral arterial pressure increases for some reason, such as, for example, the artery is constricted or narrows, or the flexibility or pliability of the artery decreases becoming stiffer, the ventricle continues to attempt to pump the same volume of blood into the artery, but, because of the increased peripheral pressure, not all of the same blood volume can pass into the artery. Instead, following the principles of conservation of energy, rather than simply stopping and amassing at the transition point, a reflection wave or backflow occurs, pushing blood back into the ventricle. The size and speed of this reflection wave is determined by the amount of peripheral pressure or the size differential of the impedance mismatch. For example, at a normal diameter, the peripheral arterial pressure may only result in a small, slow reflection wave. However, when the diameter is narrowed or constricted significantly, the peripheral arterial pressure may cause a large, fast reflection wave to backflow into the ventricle. Similarly, a pliable arterial wall may result in a normal peripheral pressure yielding a small, slow reflection wave, while a stiffened arterial wall would result in higher peripheral pressure yielding a larger, faster reflection wave.

Based on this physical response to the condition of the arterial physiology, analysis of the measured S waveform 500 will determine a value that represents the peripheral arterial pressure. The IMD detects the measured S waveform 500 and, using the peaks 501 and 502 of the two wave crest, calculates a reflection time, RT 503, between the main wave with the peak 501 and the reflection wave with the peak 502. This RT 503 is then recorded as the peripheral arterial pressure value for this measurement point.

Figure 5B:
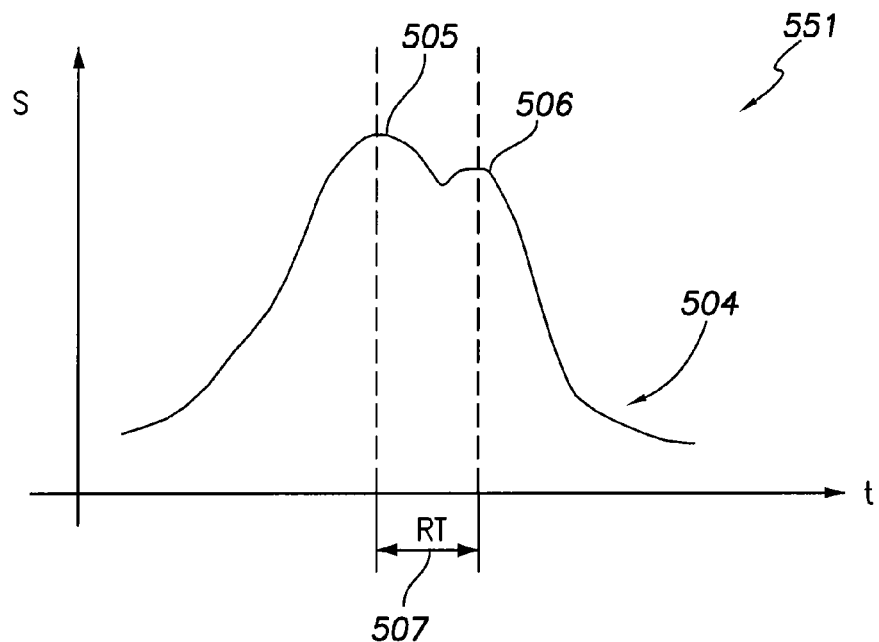
FIG. 5B is a surrogate condition graph measured by an IMD configured according to one embodiment of the present teachings.

FIG. 5B is a surrogate condition graph 551 measured by an IMD configured according to one embodiment of the present teachings. The measured S waveform 504 is taken at a different measurement time as the measured S waveform 500 (FIG. 5A). The IMD uses the main wave peak 505 and the reflection wave peak 506 to calculate the reflection time, RT 507. Compared to the RT 503 (FIG. 5A), the RT 507 is a much shorter time. The shorter reflection time represents a faster moving reflection wave. The faster reflection wave corresponds to a greater peripheral arterial pressure or greater impedance mismatch with the artery. The IMD will then record the RT 507 as the peripheral arterial pressure value for the subsequent measurement point.

Figure 5C:
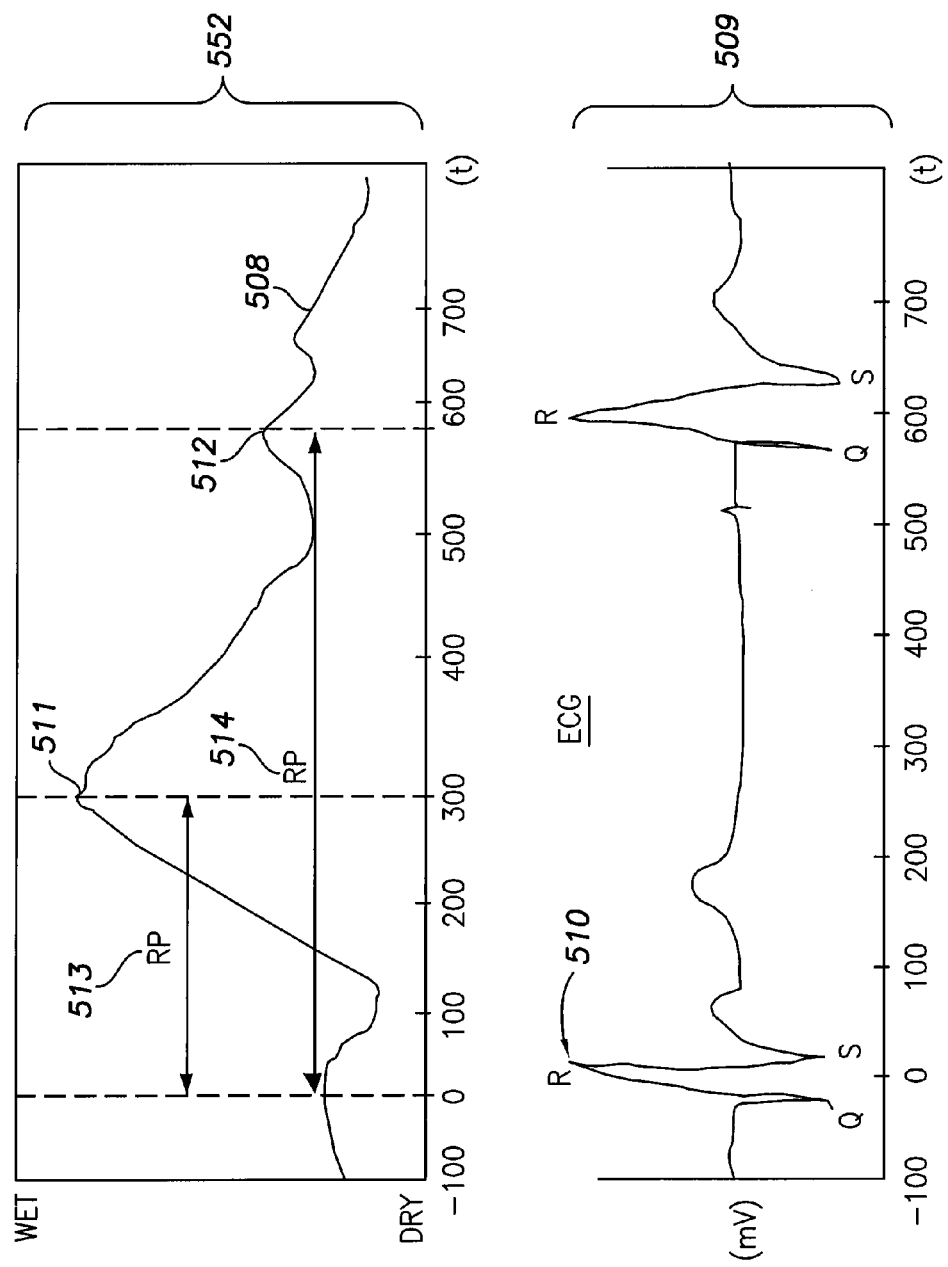
FIG. 5C shows a surrogate condition graph measured by an IMD and a corresponding electrocardiogram (ECG), configured according to one embodiment of the present teachings.

Additional methods for calculating the reflection time may be used without departing from the scope of the present teachings. FIG. 5C shows a surrogate condition graph 552 measured by an IMD and a corresponding electrocardiogram (ECG) 509, configured according to one embodiment of the present teachings. The surrogate condition graph 552 includes a measured S waveform 508. The timing axis of the surrogate condition graph 552 matches the timing axis of the ECG 509. In this example embodiment, instead of taking a direct measurement between wave peaks, the IMD takes time measurements relative to the R wave 510 of the ECG 509. The IMD, therefore, measures a relative period, RP 513, which is the relative time between the R wave 510 and the main wave peak 511, and a relative period, RP 514, which is the relative time between the R wave 510 and the reflection wave peak 512. The IMD then calculates the reflection time by subtracting RP 513 from RP 514. The calculated reflection time would then be recorded as the peripheral arterial pressure value for this measurement point.

The measurement and analysis of the surrogate condition to obtain the representative values for cardiac wall stiffness and peripheral arterial pressure provide the data that the IMD will analyze to determine the appropriate RPC setting to select. The analysis of this data is accomplished by generating a plot of the cardiac wall stiffness values against the peripheral arterial pressure values over a predetermined measurement period. The relationship of the plotted data provides an indication of the VA coupling. Moreover, the cardiac performance and physiology may then be used to select the appropriate RPC setting based on the location and orientation of this VA coupling plot.

Figure 6:
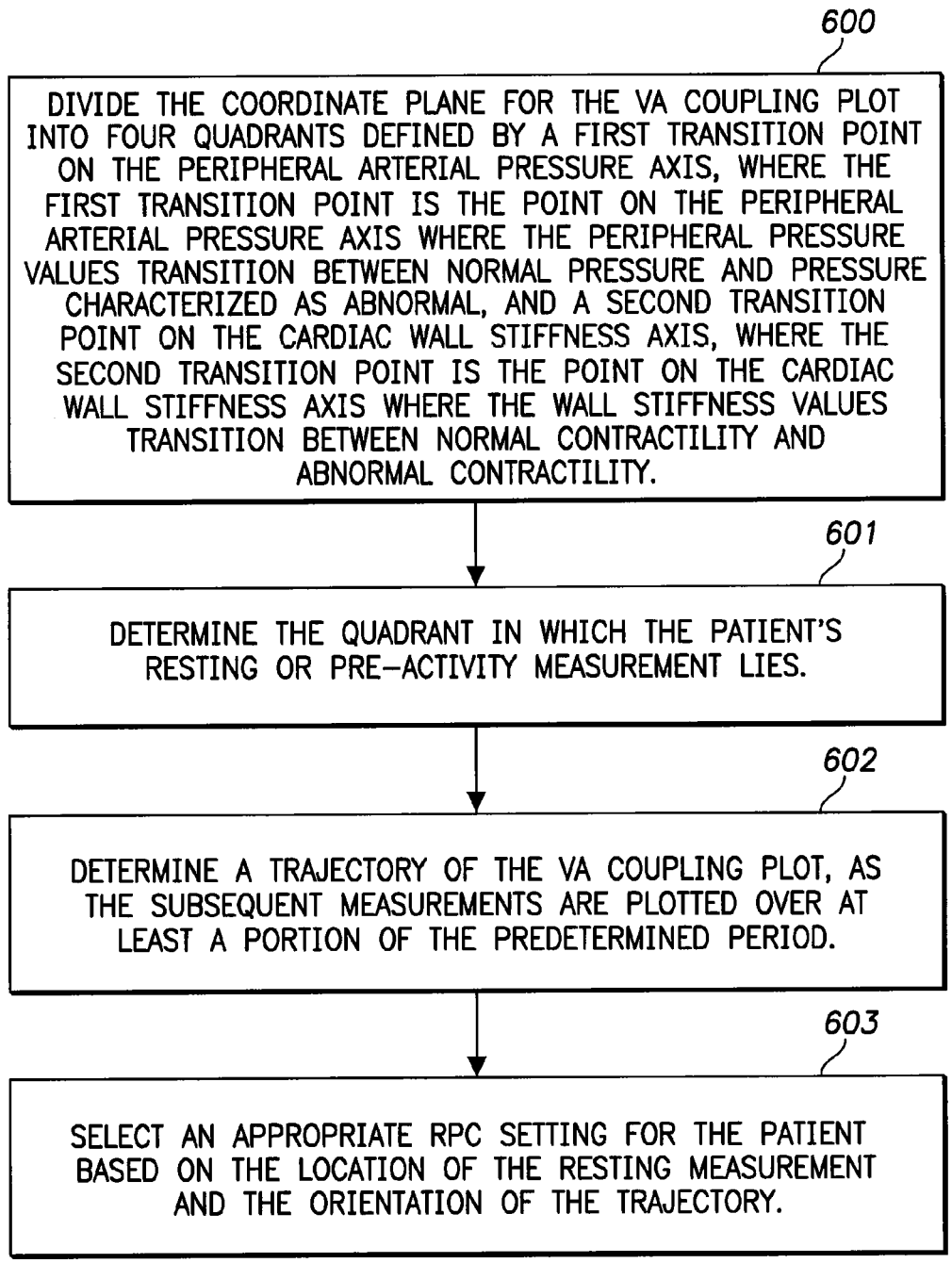
FIG. 6 is a functional block diagram illustrating functional blocks included in one embodiment of the present teachings.

FIG. 6 is a functional block diagram illustrating functional blocks included in one embodiment of the present teachings. The functional block diagram provides the function implemented by a compatible IMD in generating the VA coupling plot. In block 600, the coordinate plane for the VA coupling plot is divided into four quadrants defined by a first transition point on the peripheral arterial pressure axis and a second transition point on the cardiac wall stiffness axis. The first transition point is the point on the peripheral arterial pressure axis where the peripheral pressure values transition between normal pressure and pressure characterized as stiff. Similarly, the second transition point is the point on the cardiac wall stiffness axis where the wall stiffness values transition between normal contractility and stiff contractility. In block 601, the IMD determines the quadrant in which the patient's resting or pre-activity measurement lies. As the subsequent measurements are plotted onto the VA coupling plot over at least a portion of the predetermined period, the IMD determines a trajectory of the VA coupling plot in block 602. Based on the location of the resting measurement and the orientation of the trajectory, the IMD selects an appropriate RPC setting for the patient in block 603.

Figure 7:
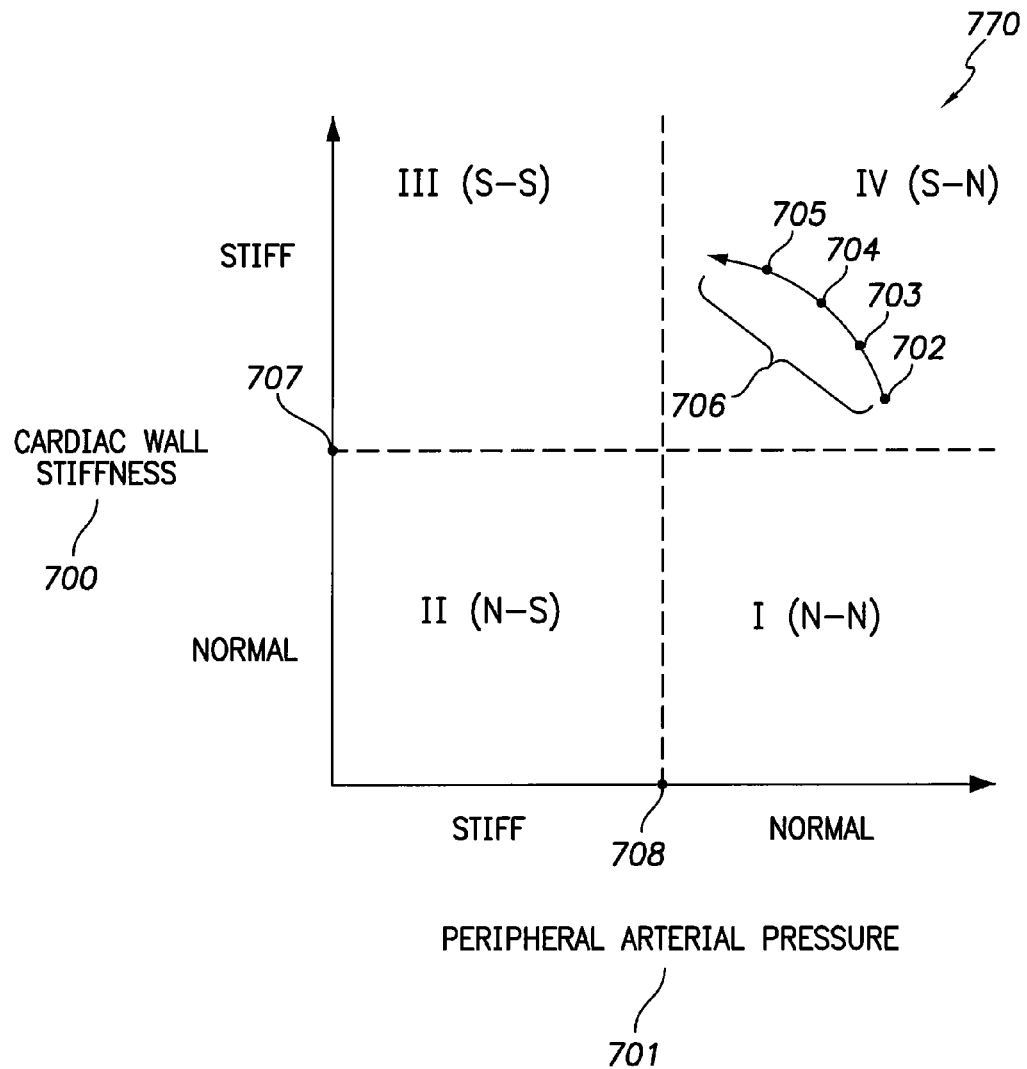
FIG. 7 is a diagram illustrating a VA coupling coordinate plane and an exemplary trajectory of VA coupling established by an IMD configured according to one embodiment of the present teachings.

Turning now to FIG. 7, a diagram is shown illustrating a VA coupling coordinate plane 770 and an exemplary trajectory of VA coupling established by an IMD configured according to one embodiment of the present teachings. The VA coupling coordinate plane 770 is defined by a cardiac wall stiffness axis 700 and an peripheral arterial pressure axis 701. The coordinate plane 770 is divided into four quadrants at transition point 707, on the cardiac wall stiffness axis 700, and transition point 708, on the peripheral arterial pressure axis 701.

Transition point 707 separates the possible cardiac wall stiffness values between normal and stiff contractility values, while transition point 708 separates the possible peripheral arterial pressure values between normal and stiff peripheral pressure values. Quadrant I (N-N) defines the coordinates in which both the contractility values and the peripheral arterial pressure values fall into the normal range. Quadrant II (N-S) defines the coordinates in which the contractility values fall into the normal range, but the peripheral pressure values fall into the stiff range. Quadrant III (S-S) defines the coordinates in which the contractility values and the peripheral pressure values both fall into the stiff range. Finally, quadrant IV (S-N) defines the coordinates in which the contractility values fall into the stiff range, while the peripheral pressure values fall into the normal range.

As an IMD detects the patient increasing activity, either through an accelerometer or other such motion detecting device, a first VA coupling measurement is taken that represents the patient at a resting state. The VA coupling measurement includes the calculated contractility value and calculated peripheral pressure value determined from measurement of a surrogate condition. This resting state measurement 702 is plotted onto the VA coupling coordinate plane 770. The IMD will continue making VA coupling measurements and plotting those exercise state measurements onto the VA coupling coordinate plane 770 for a predetermined period of time. The VA coupling coordinate plane 770 illustrates exercise state measurements 703-705, which represent the measurements made by IMD over only a portion of the predetermined period. Having only plotted the resting state measurement 702 and the exercise state measurements 703-705, the IMD analyzes the line formed by each of the plotted points to determine a trajectory 706 of the current VA coupling plot. Using the quadrant location of the resting state measurement 702 and the slope of the trajectory 706, the IMD can make a selection for an RPC setting.

In the example VA coupling plot illustrated in FIG. 7, the resting state measurement 702 lies in quadrant IV (S-N) which indicates that cardiac/ventricular wall may be a little stiff with less contractility. However, the peripheral arterial pressure remains compliant in the normal state. Moreover, the trajectory 706 rises at close to a unitary slope, which suggests that the frequency-force relationship follows the Treppe effect to some degree. The trajectory 706 also indicates that the VA coupling relationship may enter quadrant III (S-S) during continued exercise, so, while the location of the resting state measurement 702 and the slope of the trajectory 706 would suggest that the patient would respond to RPC treatment, the fact that the patient will also likely experience increased peripheral arterial pressure resistance, would indicate to the IMD to select a lower or middle setting. The IMD will often have RPC settings of minimum, medium, aggressive, and disable. In one embodiment, a higher slope (for reaction time) and more negative slope (for recovery time) of the pacing rate with respect to time (i.e., rate increase for any given time), corresponds to an aggressive RPC setting. A medium slope (for reaction time and medium negative slope for recovery time) corresponds to a medium RPC setting. A minimum RPC setting corresponds to a lower slope (for reaction time and less negative slope for recovery time). In other words, the higher the slope, the more aggressive the RPC setting for reaction time; and the more negative the slope, the more aggressive the RPC setting for recovery time. A disable setting would disable treatment altogether. Based on the location and orientation of the example VA coupling plot of FIG. 7, the IMD would likely select the medium setting.

In a normal heart, the resting measurement and, at least, the majority of the exercise state measurements will reside in quadrant I (N-N) with an orientation having a near unitary slope (i.e., a slope of nearly |1|:|1|). The IMD of such patients would, therefore, selected the aggressive RPC setting. The further away from normal the VA coupling plot is, the lower the RPC setting the IMD will select. Furthermore, more extreme orientations of the VA coupling plot, in which the slope may be very high or very low, indicate a more severe VA coupling mismatch. Such patients will likely not respond well to RPC treatment, and, therefore, the IMD would select the disable setting to disable RPC completely.

The IMD maintains storage of the various VA coupling plots generated as the patient exercises or becomes active. This stored history, such as the VA coupling history table 123 (FIG. 1), is periodically displayed to a physician or IMD technician using a special external device that establishes communication with the IMD unit. The VA coupling history provides the information that a physician can use to establish appropriate medication and/or exercise regimens specifically customized for the patient's condition.

Figure 8:
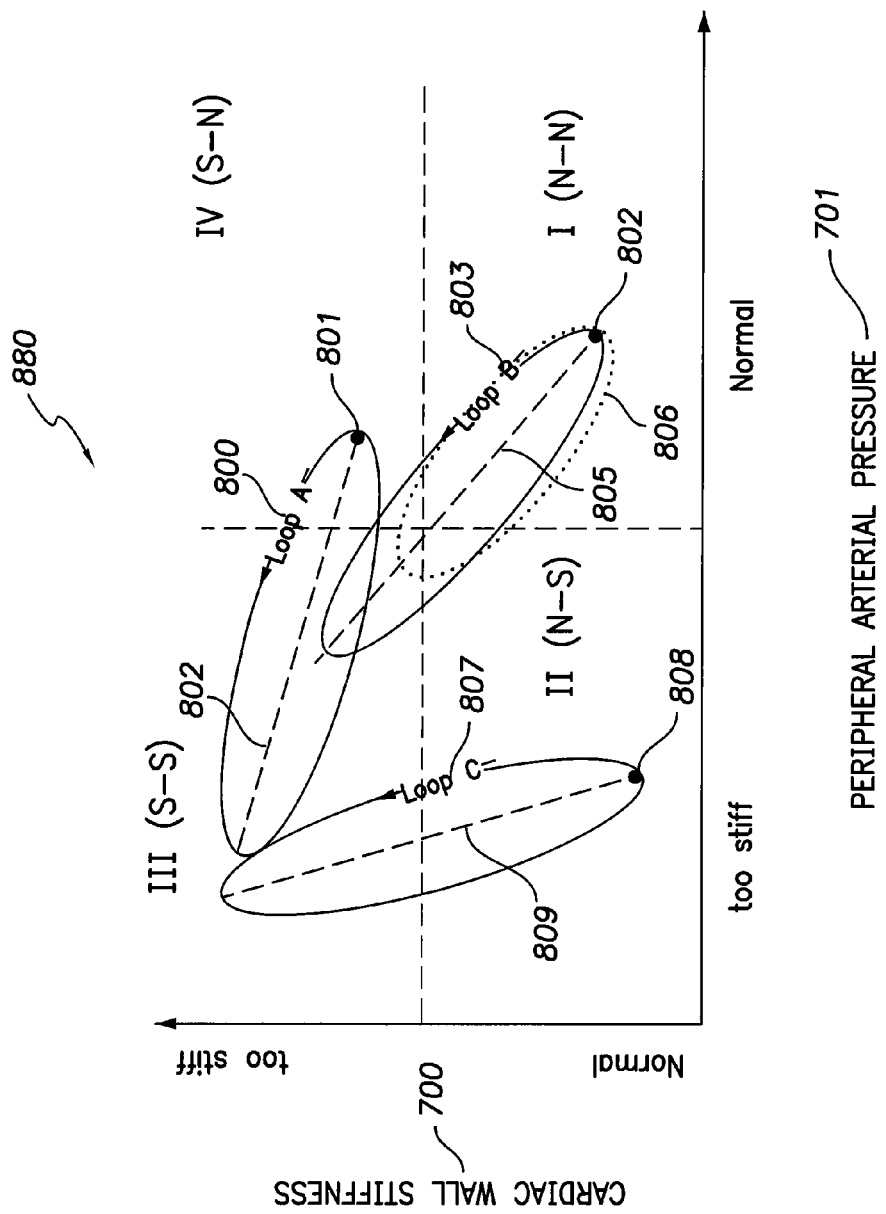
FIG. 8 is a chart illustrating a VA coupling coordinate plane and exemplary trajectories of VA coupling as generated by an IMD configured according to one embodiment of the present teachings.

FIG. 8 is a chart illustrating a VA coupling history table 880 and exemplary trajectories of VA coupling as generated and stored by an IMD configured according to one embodiment of the present teachings. The VA coupling history table 880 includes the recorded measurements (i.e., estimates) for multiple VA coupling plots taken over time. The coordinate plane is defined by the cardiac wall stiffness axis 700 and the peripheral arterial pressure axis 701, as described with respect to the VA coupling coordinate plane 770 (FIG. 7). The VA coupling history table 880 includes VA coupling plots 800, 803, and 807. The VA coupling plot 800 begins with the resting state measurement 801. This represents the starting point from when an increased activity level of the patient is detected. Plotting the contractility measurements against the peripheral pressure measurements over the entire course of elevated activity will result in a loop plot. Beginning exercise or activity will cause a faster rise in the VA reactions up through the end of the exercise. Once the exercise is finished, the VA reaction and performance will more slowly decay back to the resting state measurement 801. The loop shape of VA coupling plots 800, 803, and 807 are analyzed using the quadrant locations of the resting state measurements 801, 804, and 808, the quadrant locations in which any part of the plots enter, and the general slopes 802, 805, and 809 of the plots' trajectories. Using this information, the physician can determine the level of VA coupling experienced by the patient and the relative physiologies of the cardiac and arterial walls. This diagnosis information may then be used to establish specific medication and exercise regimens for the patient.

For example, the VA plot 800 has its resting state measurement 801 within quadrant IV (S-N), thus, indicating that the patient's ventricular wall has a reduced contractility. However, the general slope 802 of the VA plot 800 is close to unitary, which indicates a near healthy force-frequency relationship. The general slope 802 also shows that the ventricular wall stiffness does not increase too much over the course of exercise. Therefore, the patient would likely benefit from continued RPC treatment at a medium setting. The VA plot 803 has its resting state measurement 804 within quadrant I (N-N), thus, indicating a normal ventricular stiffness and peripheral pressure. The general slope 805 is also nearly, if not exactly, unitary, which indicates a healthy and normal force-frequency relationship. The extreme portions of the VA plot 803 move through the other quadrants II (N-S), III (S-S), and IV (S-N). Therefore, a physician may conclude that an aggressive RPC setting and a strong exercise routine may benefit the patient. The VA plot 803 closely resembles the normal VA plot 806. The aggressive RPC setting and strong exercise routine would help the patient's VA coupling performance to get more in line with the normal VA plot 806 by reducing the more extreme response as the VA coupling response improves.

The VA plot 807 has its resting state measurement 808 within quadrant II (N-S), thus, indicating that the patient's arterial wall is either stiff or narrowed to the point where the peripheral pressure is greater than normal. Moreover, the general slope 809 of the VA plot 807 is very high. The extreme slope indicates a poor force-frequency relationship which is a determination of a VA coupling mismatch. This mismatch indicates to the physician that the patient may not respond well to either an RPC treatment or to exercise without proper medication. The VA coupling history table 880, therefore, provides valuable historic information to a physician in order to monitor a patient's progress and proscribe appropriate medications and exercise regimens.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2A) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine or computer readable medium tangibly embodying instructions that may be in a form implantable or coupled to an implantable medical device may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored.

The machine or computer readable medium that stores the software code defining the methodologies and functions described herein includes physical computer storage media. A storage medium may be any available medium that can be accessed by the processor of an implantable medical device. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed is:

1. A method for selecting a rate programming control (RPC) setting in an implantable medical device (IMD), said method comprising:
   detecting, by the IMD, an increase in activity for a patient having said IMD;
   estimating, by the IMD, a cardiac wall stiffness over a predetermined period;
   estimating, by the IMD, a peripheral arterial pressure over said predetermined period; and
   responsive to the estimated cardiac wall stiffness and estimated peripheral arterial pressure, selecting, by the IMD, said RPC setting.

2. The method of claim 1 wherein said estimating said cardiac wall stiffness and said estimating said peripheral arterial pressure comprise:
   measuring a ventricular-arterial (VA) coupling surrogate condition;
   analyzing said measured VA coupling surrogate condition for indications of cardiac wall stiffness; and
   analyzing said measured VA coupling surrogate condition for indications of peripheral arterial pressure.

3. The method of claim 2 wherein said VA coupling surrogate condition comprises at least one of:
   cardiogenic impedance;
   blood pressure; and
   a pulsatile component of a photoplethysmograph (PPG).

4. The method of claim 2 wherein said analyzing said measured VA coupling surrogate condition for indications of cardiac wall stiffness comprises:
   determining a slope of a waveform representing said measured VA coupling surrogate condition; and
   wherein said analyzing said VA coupling surrogate condition for indications of peripheral arterial pressure comprises:
   measuring a reflection time between a forward wave component of said waveform and a reflection wave component of said waveform.

5. The method of claim 1, further comprising generating a ventricular-arterial (VA) coupling plot of said estimated cardiac wall stiffness values against said estimated peripheral arterial pressure values; and selecting the RPC setting based on a location and an orientation of said VA coupling plot.

6. The method of claim 5 wherein said generating said VA coupling plot comprises:
- dividing a coordinate plane for said VA coupling plot into four quadrants, said four quadrants defined by a first transition point on an peripheral arterial pressure axis of said coordinate plane where peripheral pressure values transition between normal pressure and abnormal pressure, and a second transition point on a cardiac wall stiffness axis of said coordinate plane where wall stiffness values transition between normal contractility and abnormal contractility;
- determining which quadrant of said four quadrants in which a resting VA coupling point lies; and
- determining a trajectory of said VA coupling plot as said estimated cardiac wall stiffness values are plotted against said estimated peripheral arterial pressure values for at least a portion of said predetermined period;
- wherein said selecting said RPC setting is based on said location of said quadrant in which said resting VA coupling point lies and said orientation of a slope of said trajectory.

7. The method of claim 5 further comprising:
- storing said VA coupling plot and a plurality of subsequent VA coupling plots generated for corresponding subsequent instances of increased activity into an VA coupling history table; and
- transmitting said VA coupling history table for display to a physician for determination of medical treatment for said patient.

8. An implantable medical device (IMD) comprising:
an activity sensor;
at least one cardiac pacing lead;
at least one ventricular-arterial (VA) coupling surrogate condition sensor;
a programmable microcontroller coupled to said activity sensor, to said at least one cardiac pacing lead, and to said at least one VA coupling surrogate condition sensor, wherein said programmable microcontroller controls operation of said IMD;
a memory coupled to said programmable microcontroller;
a VA coupling surrogate analysis module stored on said memory, wherein, when executed by said programmable microcontroller, said VA coupling surrogate analysis module configures said IMD:
- to activate said activity sensor to detect an increase in activity of a patient;
- to activate said at least one VA coupling surrogate condition sensor:
  - to estimate a cardiac wall stiffness over a predetermined period; and
  - to estimate an peripheral arterial pressure over said predetermined period;
- to generate a VA coupling plot of said estimated cardiac wall stiffness values against said estimated peripheral arterial pressure values; and
- to select a rate programming control (RPC) setting based on a location and an orientation of said VA coupling plot.

9. The IMD of claim 8 wherein said executing VA coupling surrogate analysis module further configures said at least one VA coupling surrogate condition sensor to estimate said cardiac wall stiffness and to estimate said peripheral arterial pressure through:
measurement of a VA coupling surrogate condition;
analysis of said measured VA coupling surrogate condition for indications of cardiac wall stiffness; and
analysis of said measured VA coupling surrogate condition for indications of peripheral arterial pressure.

10. The IMD of claim 9 wherein said VA coupling surrogate condition comprises at least one of:
cardiogenic impedance;
blood pressure; and
a pulsatile component of a photoplethysmograph (PPG).

11. The IMD of claim 9 wherein said executing VA coupling surrogate analysis module further configures said at least one VA coupling surrogate condition sensor analyzing said VA coupling surrogate condition for indications of said cardiac wall stiffness:
- to determine a slope of a waveform representing said measured VA coupling surrogate condition;
- wherein said executing VA coupling surrogate analysis module further configures said at least one VA coupling surrogate condition sensor analyzing said VA coupling surrogate condition for indications of peripheral arterial pressure:
- to measure a reflection time between a forward wave component of said waveform and a reflection wave component of said waveform; and
- wherein said executing VA coupling surrogate analysis module further configures said IMD generating said VA coupling plot:
- to plot said slope of said waveform against said reflection time.

12. The IMD of claim 8 wherein said executing VA coupling surrogate analysis module further configures said IMD generating said VA coupling plot:
- to divide a coordinate plane for said VA coupling plot into four quadrants, said four quadrants defined by a first transition point on an peripheral arterial pressure axis of said coordinate plane where peripheral pressure values transition between normal pressure and abnormal pressure, and a second transition point on a cardiac wall stiffness axis of said coordinate plane where wall stiffness values transition between normal contractility and abnormal contractility;
- to determine which quadrant of said four quadrants in which a resting VA coupling point lies; and
- to determine a trajectory of said VA coupling plot as said estimated cardiac wall stiffness values are plotted against said estimated peripheral arterial pressure values for at least a portion of said predetermined period;
- wherein said selection of said RPC setting is based on said location of said quadrant in which said resting VA coupling point lies and said orientation of a slope of said trajectory.

13. The IMD of claim 8 wherein said RPC setting comprises one of:
disabled;
minimum RPC;
medium RPC; and
aggressive RPC.

14. The IMD of claim 8 wherein said executing VA coupling surrogate analysis module further configures said IMD:
- to store said VA coupling plot and a plurality of subsequent VA coupling plots generated for corresponding subsequent instances of increased activity into an VA coupling history table on said memory; and
- to transmit said VA coupling history table for display to a physician for determination of medical treatment for said patient.

15. A system for selecting a rate programming control (RPC) setting in an implantable medical device (IMD), said system comprising:

means for detecting an increase in activity for a patient having said IMD;

means for estimating a cardiac wall stiffness over a predetermined period;

means for estimating an peripheral arterial pressure over said predetermined period;

means for generating an ventricular-arterial (VA) coupling plot of said estimated cardiac wall stiffness values against said estimated peripheral arterial pressure values; and means, executable responsive to a location and an orientation of said VA coupling plot, for selecting said RPC setting.

16. The system of claim 15 wherein said means for estimating said cardiac wall stiffness and said means for estimating said peripheral arterial pressure comprise:

means for measuring a VA coupling surrogate condition;

means for analyzing said measured VA coupling surrogate condition for indications of cardiac wall stiffness; and means for analyzing said measured VA coupling surrogate condition for indications of peripheral arterial pressure.

17. The system of claim 16 wherein said VA coupling surrogate condition comprises at least one of:

cardiogenic impedance;

blood pressure; and a pulsatile component of a photoplethysmograph (PPG).

18. The system of claim 16 wherein said means for analyzing said measured VA coupling surrogate condition for indications of cardiac wall stiffness comprises:

means for determining a slope of a waveform representing said measured VA coupling surrogate condition;

wherein said means for analyzing said VA coupling surrogate condition for indications of peripheral arterial pressure comprises:

means for measuring a reflection time between a forward wave component of said waveform and a reflection wave component of said waveform; and said means for generating said VA coupling plot comprises:

means for plotting said slope of said waveform against said reflection time.

19. The system of claim 15 wherein said means for generating said VA coupling plot comprises:

means for dividing a coordinate plane for said VA coupling plot into four quadrants, said four quadrants defined by a first transition point on an peripheral arterial pressure axis of said coordinate plane where peripheral pressure values transition between normal pressure and abnormal pressure, and a second transition point on a cardiac wall stiffness axis of said coordinate plane where wall stiffness values transition between normal contractility and abnormal contractility;

means for determining which quadrant of said four quadrants in which a resting VA coupling point lies; and means for determining a trajectory of said VA coupling plot as said estimated cardiac wall stiffness values are plotted against said estimated peripheral arterial pressure values for at least a portion of said predetermined period;

wherein said means for selecting said RPC setting is based on said location of said quadrant in which said resting VA coupling point lies and said orientation of a slope of said trajectory.

20. The system of claim 15 further comprising:

means for storing said VA coupling plot and a plurality of subsequent VA coupling plots generated for corresponding subsequent instances of increased activity into an VA coupling history table; and means for transmitting said VA coupling history table for display to a physician for determination of medical treatment for said patient.

\* \* \* \* \*